(12) United States Patent
Kabir et al.

(10) Patent No.: US 9,557,252 B2
(45) Date of Patent: Jan. 31, 2017

(54) FABRIC PHASE SORPTIVE EXTRACTORS

(71) Applicants: Abuzar Kabir, Dacca (BD); Kenneth G. Furton, Homestead, FL (US)

(72) Inventors: Abuzar Kabir, Dacca (BD); Kenneth G. Furton, Homestead, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/069,430

(22) Filed: Mar. 14, 2016

(65) Prior Publication Data
US 2016/0223440 A1 Aug. 4, 2016

Related U.S. Application Data

(63) Continuation of application No. 14/216,121, filed on Mar. 17, 2014, now Pat. No. 9,283,544.

(60) Provisional application No. 61/787,910, filed on Mar. 15, 2013.

(51) Int. Cl.
| | |
|---|---|
| *B01J 20/26* | (2006.01) |
| *G01N 1/40* | (2006.01) |
| *B01J 20/32* | (2006.01) |
| *B01J 20/291* | (2006.01) |
| *G01N 1/02* | (2006.01) |
| *B01J 20/22* | (2006.01) |
| *G01N 33/94* | (2006.01) |

(52) U.S. Cl.
CPC ............. *G01N 1/405* (2013.01); *B01J 20/223* (2013.01); *B01J 20/291* (2013.01); *B01J 20/3225* (2013.01); *B01J 20/3289* (2013.01); *B01J 20/3295* (2013.01); *G01N 1/02* (2013.01); *G01N 33/94* (2013.01); *G01N 2001/028* (2013.01)

(58) Field of Classification Search
CPC .................................. B01J 20/26; B01J 20/22
USPC ........................................ 502/402, 401, 526
See application file for complete search history.

(56) References Cited

U.S. PATENT DOCUMENTS

| | | |
|---|---|---|
| 5,496,741 A | 3/1996 | Pawliszyn |
| 5,565,622 A | 10/1996 | Murphy |
| 5,576,217 A | 11/1996 | Hsu |
| 5,691,206 A | 11/1997 | Pawliszyn |
| 6,042,787 A | 3/2000 | Pawliszyn |
| 6,164,144 A | 12/2000 | Berg |
| 6,405,608 B1 | 6/2002 | Lindgren et al. |
| 6,481,301 B2 | 11/2002 | Pawliszyn |
| 6,645,908 B1 | 11/2003 | Sigman et al. |
| 6,759,126 B1 | 7/2004 | Malik et al. |
| 6,783,680 B2 | 8/2004 | Malik |
| 6,815,216 B2 | 11/2004 | Sandra et al. |
| 6,825,046 B1 | 11/2004 | Forsyth |
| 6,929,778 B2 | 8/2005 | Nunes et al. |
| 6,998,040 B2 | 2/2006 | Malik et al. |
| 7,125,580 B2 | 10/2006 | Miller et al. |
| 7,404,932 B2 | 7/2008 | Chen et al. |
| 7,464,614 B2 | 12/2008 | Harvey |
| 7,622,191 B2 | 11/2009 | Malik et al. |
| 7,645,611 B2 | 1/2010 | Pawliszyn |
| 7,665,374 B2 | 2/2010 | Akinbo et al. |
| 7,674,631 B2 | 3/2010 | Pawliszyn |
| 7,776,615 B2 | 8/2010 | Yuka et al. |
| 8,104,331 B2 | 1/2012 | Pawliszyn et al. |
| 8,230,703 B2 | 7/2012 | Alizadeh et al. |
| 8,241,476 B1 | 8/2012 | Malik et al. |
| 9,283,544 B2 * | 3/2016 | Kabir .................. B01J 20/3295 |
| 2004/0241874 A1 | 12/2004 | Abdel-Rehim |

* cited by examiner

*Primary Examiner* — Edward Johnson
(74) *Attorney, Agent, or Firm* — Saliwanchik, Lloyd & Eisenschenk

(57) ABSTRACT

A fabric phase sorptive extractor (FPSE) is a sampling device where a flexible fabric is coated with at least one sol-gel derived film that includes at least two of a metal oxide portion, a siloxy portion, and an organic portion, where the gel has at least some amorphous portions. The FPSE is flexible such that it can be used in an extended form or draped over a solid surface to contact a gaseous, liquid, or solid environment and can be manipulated for placement in a container where the absorbed analyte can be removed from the FPSE for instrumental analysis. The FPSE can have specific functionalities that bind to specific analytes or can provide a general sorbent medium for extraction of a wide range of analytes, such that the sampling device can be employed for sampling analytes with biological, environmental, food, pharmaceutical, bio-analytical, clinical, forensic, toxicological, national security, public health, and/or safety implications.

22 Claims, 14 Drawing Sheets

| 100 ppb | Day 1 | | Day 2 | | Day 3 | | Overall |
|---|---|---|---|---|---|---|---|
| Compound | Avg. | % RSD | Avg. | % RSD | Avg. | % RSD | % RSD |
| 1,3,5-TNB | 5.0 | 1.6 | 4.5 | 3.8 | 4.7 | 2.7 | 2.7 |
| 1,3-DNB | 9.1 | 2.7 | 8.6 | 2.0 | 8.7 | 3.5 | 2.7 |
| NB | 8.7 | 2.5 | 8.5 | 4.8 | 8.9 | 1.1 | 2.8 |
| TNT | 11.5 | 1.8 | 11.3 | 4.4 | 11.6 | 1.2 | 2.5 |
| Tetryl | 8.2 | 2.1 | 7.9 | 2.6 | 8.2 | 5.6 | 3.4 |
| 2,6-DNT | 8.7 | 2.9 | 8.2 | 0.7 | 8.5 | 4.6 | 2.7 |
| 2-NT | 7.4 | 5.7 | 6.8 | 1.5 | 6.5 | 4.0 | 3.7 |
| 4-NT | 7.7 | 5.3 | 7.1 | 1.6 | 7.0 | 6.5 | 4.4 |
| 3-NT | 9.0 | 6.4 | 8.2 | 3.7 | 8.0 | 4.1 | 4.7 |
| 4-am-2,6-DNT | 9.4 | 7.0 | 9.5 | 0.6 | 9.1 | 6.3 | 4.6 |
| 2-am-4,6-DNT | 13.5 | 7.4 | 12.8 | 3.4 | 13.8 | 5.0 | 5.3 |
| | 8.9 | 4.1 | 8.5 | 2.7 | 8.6 | 4.1 | 3.6 |

*Figure 11*

| | Reproducibility between Fabric Phase Sorptive Extractors | | | | | | |
|---|---|---|---|---|---|---|---|
| Compound | FPSE 1 | FPSE 2 | FPSE 3 | FPSE 4 | FPSE 5 | Avg. | % RSD |
| 1,3,5-TNB | 4.7 | 5.1 | 5.6 | 5.6 | 4.8 | 5.2 | 8.3 |
| 1,3-DNB | 8.9 | 9.1 | 8.9 | 8.9 | 8.9 | 8.9 | 1.0 |
| NB | 8.8 | 9.1 | 8.6 | 9.0 | 9.2 | 8.9 | 2.7 |
| TNT | 11.4 | 12.4 | 11.5 | 12.2 | 12.1 | 11.9 | 3.7 |
| Tetryl | 8.4 | 8.6 | 8.5 | 8.2 | 8.5 | 8.4 | 1.8 |
| 2,6-DNT | 9.0 | 9.5 | 9.8 | 9.0 | 9.2 | 9.3 | 3.7 |
| 2-NT | 6.9 | 7.3 | 7.4 | 7.1 | 7.0 | 7.1 | 2.9 |
| 4-NT | 7.5 | 7.6 | 8.0 | 7.4 | 7.7 | 7.6 | 3.0 |
| 3-NT | 8.1 | 8.9 | 9.3 | 8.7 | 9.0 | 8.8 | 5.1 |
| 4-am-2,6-DNT | 9.4 | 10.5 | 10.1 | 9.9 | 10.6 | 10.1 | 4.8 |
| 2-am-4,6-DNT | 14.4 | 14.4 | 14.3 | 13.4 | 14.4 | 14.2 | 3.1 |
| | | | | | | 9.1 | 3.6 |

*Figure 12*

| Compound | Extraction on untreated FPSE Avg. | Extraction after treating with MeCl$_2$ (8 h) Avg. | Extraction after treating with HCl solution (0.1 M, 8 h) Avg. | Extraction after treating with NaOH solution (0.1 M, 8 h) Avg. |
|---|---|---|---|---|
| 1,3,5-TNB | 1.5 | 2.6 | 2.6 | 2.1 |
| 1,3-DNB | 3.1 | 4.2 | 4.5 | 4.0 |
| NB | 3.2 | 4.4 | 4.6 | 4.4 |
| TNT | 4.2 | 5.8 | 5.7 | 5.6 |
| Tetryl | 2.8 | 4.2 | 4.1 | 2.9 |
| 2,6-DNT | 3.4 | 4.6 | 4.6 | 4.6 |
| 2-NT | 2.6 | 3.7 | 3.7 | 3.3 |
| 4-NT | 2.9 | 3.7 | 3.8 | 3.7 |
| 3-NT | 3.6 | 4.4 | 4.4 | 4.1 |
| 4-am-2,6-DNT | 4.2 | 4.6 | 5.1 | 4.6 |
| 2-am-4,6-DNT | 5.2 | 6.1 | 6.6 | 6.2 |
|  | 3.4 | 4.4 | 4.5 | 4.2 |

FABRIC PHASE SORPTIVE EXTRACTORS

CROSS-REFERENCE TO RELATED APPLICATIONS

This application is a continuation of U.S. application Ser. No. 14/216,121, filed Mar. 17, 2014, which claims the benefit of U.S. Provisional Application Ser. No. 61/787,910, filed Mar. 15, 2013, which is hereby incorporated by reference herein in its entirety, including any figures, tables, or drawings.

BACKGROUND OF INVENTION

Surface-bonded hybrid organic-inorganic polymer coatings and monolithic beds are popular sorbents for use in analytical microextraction. These systems display high chemical stability and offer a diverse array of extracting phases for solvent-free analytical sample preparation. The availability of a wide variety of sol-gel precursors and sol-gel active organic polymers allow facile synthesis of advanced material systems with unique selectivity, enhanced extraction sensitivity and high thermal, mechanical and solvent stability. These sol-gel derived hybrid organic-inorganic advanced material systems have been shown to be effective in solvent free/solvent minimized sample preparation for a wide variety of analytes with biological, environmental, clinical, toxicological, food, pharmaceutical, bioanalytical, and forensic significance.

Sol-gel technology for the preparation of solid phase microextraction (SPME) sorbents has solved many limitations of conventional coatings. Sol-gel coatings chemically bond to many different substrates, such as silica, when the gel is formed from the sol solution in the presence of the substrate. Because of the wide variety of possible sol components, sol-gel technology allows the synthesis of a large number of sorbents for SPME and similar microextraction techniques (e.g., capillary microextraction, stir bar sorptive extraction) with large surface area, unique selectivity, and high thermal and solvent stability. Sol-gel monolithic beds are capable of achieving very high sample pre-concentration factors. The versatility of sol-gel technology allows the creation of surface-bonded sorbent coatings on unbreakable fiber materials (e.g., Ni—Ti, stainless steel, titanium, and copper) and also on substrates of different geometrical formats such as planar SPME (PSPME), and membrane SPME (MSPME). Sol-gel technology is adaptable to forming multi-component materials that have customized surface morphologies, selectivities and affinities of the sorbent. A wide variety of sol-gel silica, titania, zirconia, alumina, and germania-based precursors are commercially available. Additionally, a wide range of sol-gel reactive organic ligands are available to design hybrid organic-inorganic sol-gel coatings that can be used to target a particular analyte or sample matrix with improved selectivity, sensitivity, extraction phase stability and performance.

There remains a strong need for solvent free/solvent minimized microextraction devices that permit the acquisition of very low concentrations of analytes that are present in a wide range of environments. Most microextraction devices are suited to a particular type of environment, and are often poorly suited for other environments. For example, some microextraction devices are well suited to sample air or other gases while others are suited for extraction from water or other liquids. Few are microextraction devices that can be easily adapted for sampling a solid surface. In addition, the limitation inherent to the geometric configurations of microextraction devices (smaller substrate surface area in both fiber and in-tube format) does not allow using high amount of sorbent materials for extraction. The physical immobilization of polymeric materials on the substrate surface in microextraction devices limit their exposure to high temperature for thermal desorption and to organic solvents for solvent mediated desorption. As a result, many compounds with high boiling points and high polarity are still beyond the reach of microextraction devices. Furthermore, the microextraction devices are not recommended to make direct contacts with the sample matrix when it contains high volume of particulates, debris or other matrix interferences (e.g., protein, tissues, fat molecules) that may cause irreversible damage to the sorbent coating.

SUMMARY OF THE INVENTION

Embodiments of the invention are directed to a fabric phase sorptive extractor (FPSE), where a flexible fabric that has one or more bound gel films. The gel film has a metal oxide portion, a siloxy portion, and/or an organic portion. Siloxy and organic portion are polymeric. The film is at least partially amorphous and is absorbent toward at least one target analyte. The FPSE is flexible.

Another embodiment of the invention is directed to a method of preparing a FPSE, where a flexible fabric has a sol deposited on a surface of the flexible fabric and subsequently cured to a gel network. Any unreacted portions of the sol or non-bound side products of gelation are removed from the FPSE.

Another embodiment of the invention is directed to a method of sampling a target analyte, where the FPSE is used to absorb a target analyte in the gel film of the FPSE when contacted to an environment that is suspected of containing the target analyte. After removal of the FPSE from the environment, the FPSE can be used to provide an analytical sample. The analytical sample can be removed from the FPSE and analyzed upon delivery of the analyte to a sample port of an analytical instrument.

BRIEF DESCRIPTION OF DRAWINGS

FIG. 11 is a table of the day-to-day reproducibility of extraction of various analytes using a FPSE, according to an embodiment of the invention.

FIG. 12 is a table showing the reproducibility of extraction by individual FPSEs, according to embodiments of the invention, where the FPSEs have like composition.

DETAILED DISCLOSURE

Figure 1A:
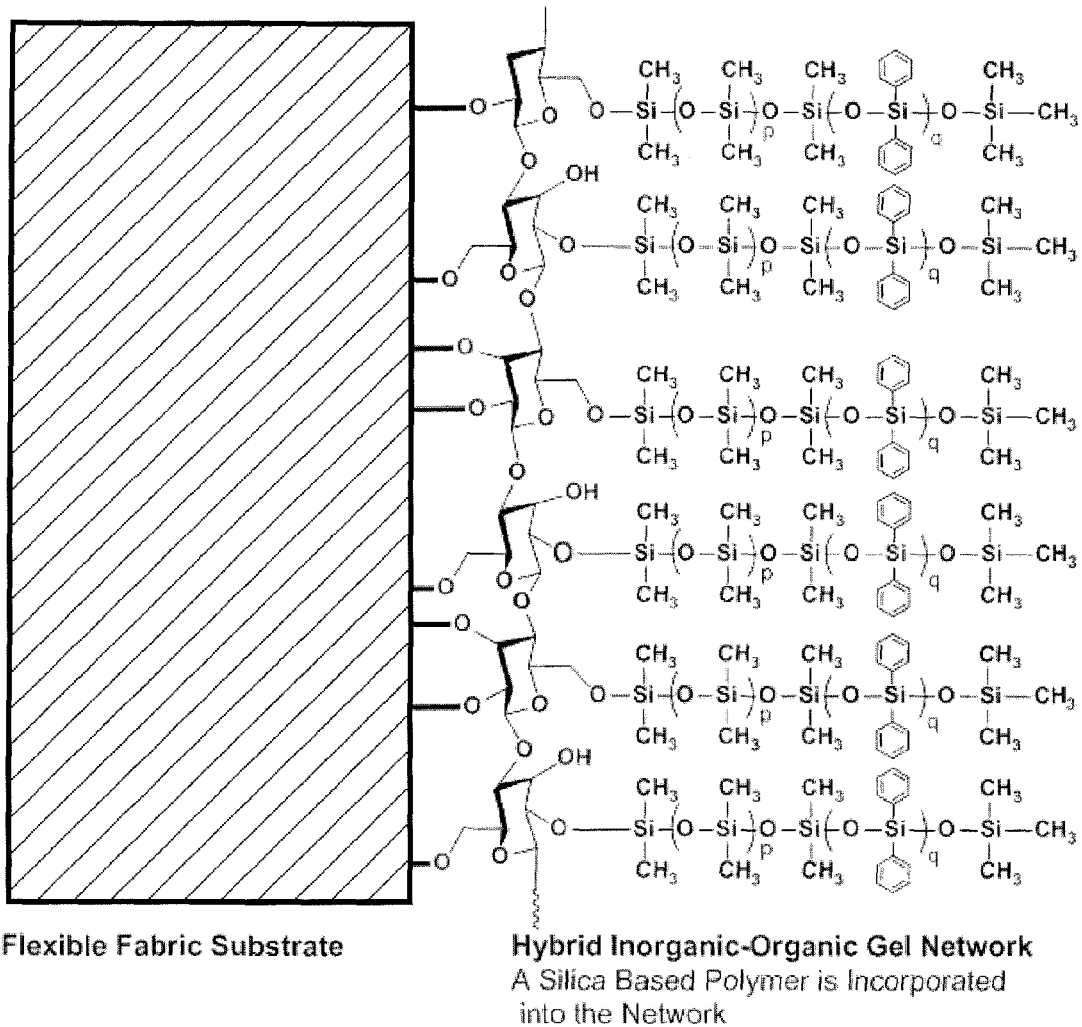
FIG. 1(A) is a schematic drawing of: a portion of an exemplary fabric phase sorptive extractor (FPSE) (100% cotton substrate), with a silica based polymer as organic additive, according to an embodiment of the invention.
Figure 1B:
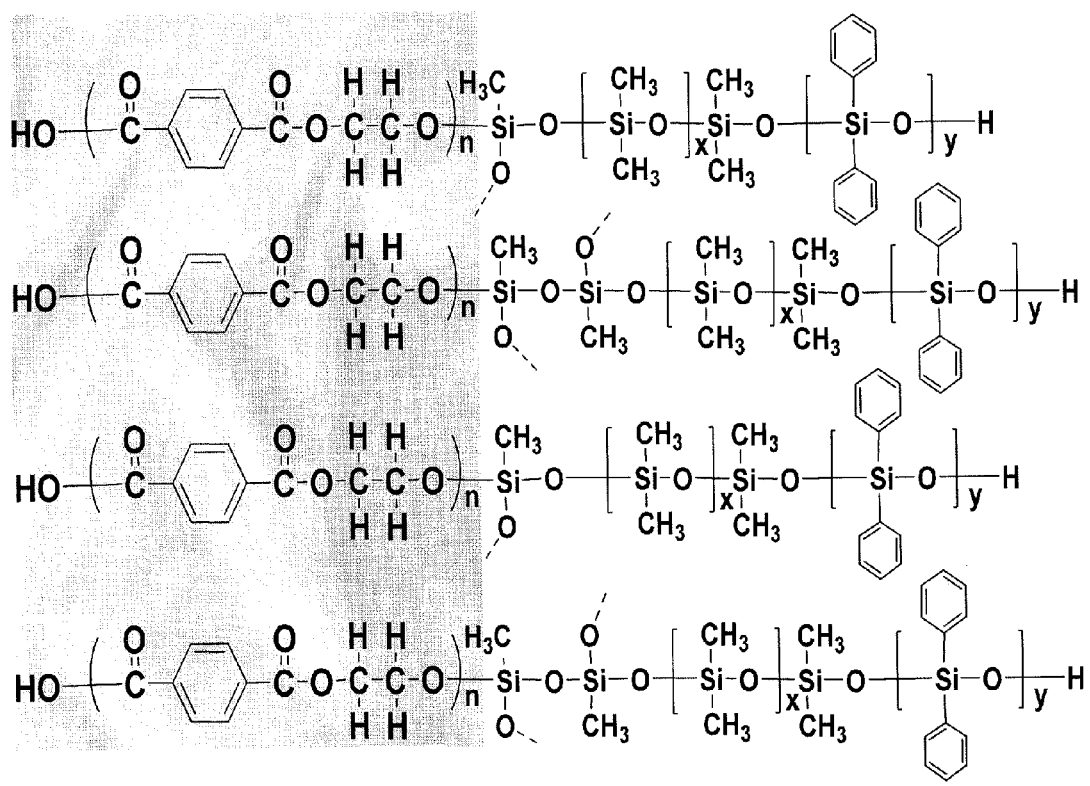
FIG. 1(B) is a schematic drawing of: a portion of an exemplary fabric phase sorptive extractor (FPSE) (100% polyester substrate) with a silica based polymer as organic additive, according to an embodiment of the invention.
Figure 2A:
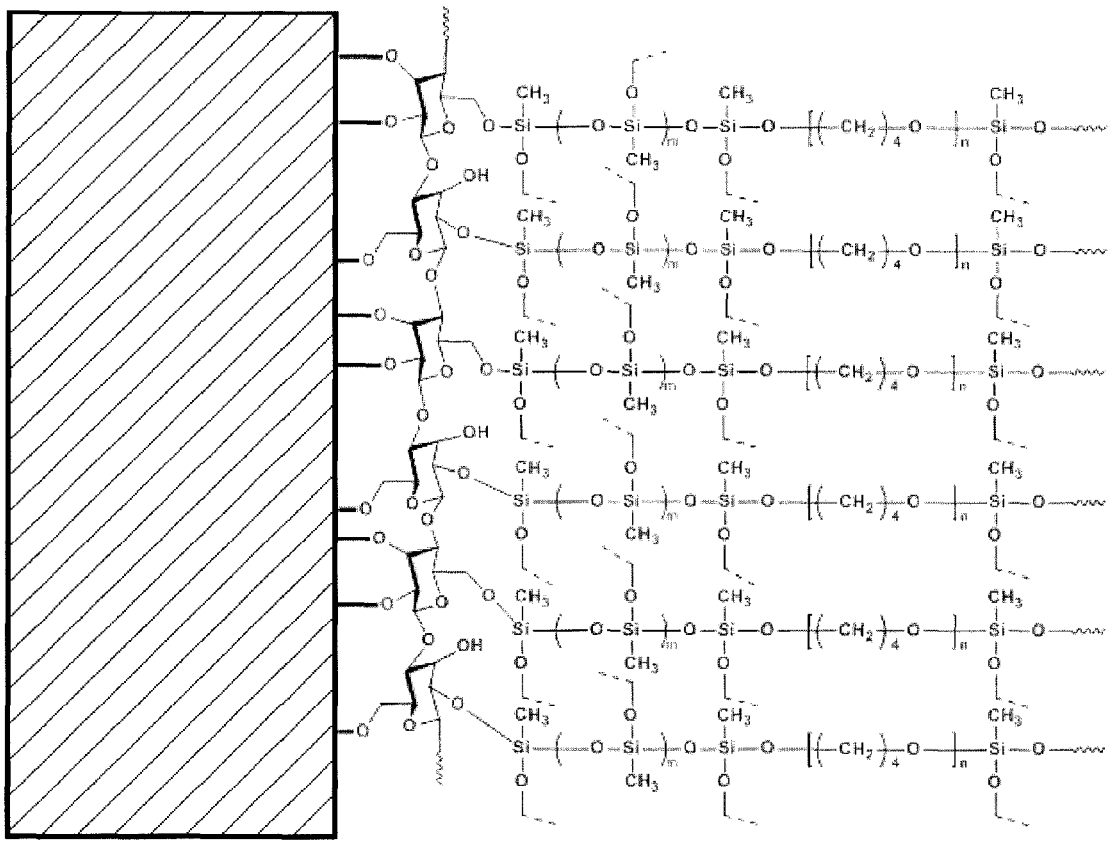
FIG. 2(A) is a schematic drawing of a portion of an exemplary fabric phase sorptive extractor (FPSE), using a non-silica based polymer as organic additive, according to an embodiment of the invention.
Figure 2B:
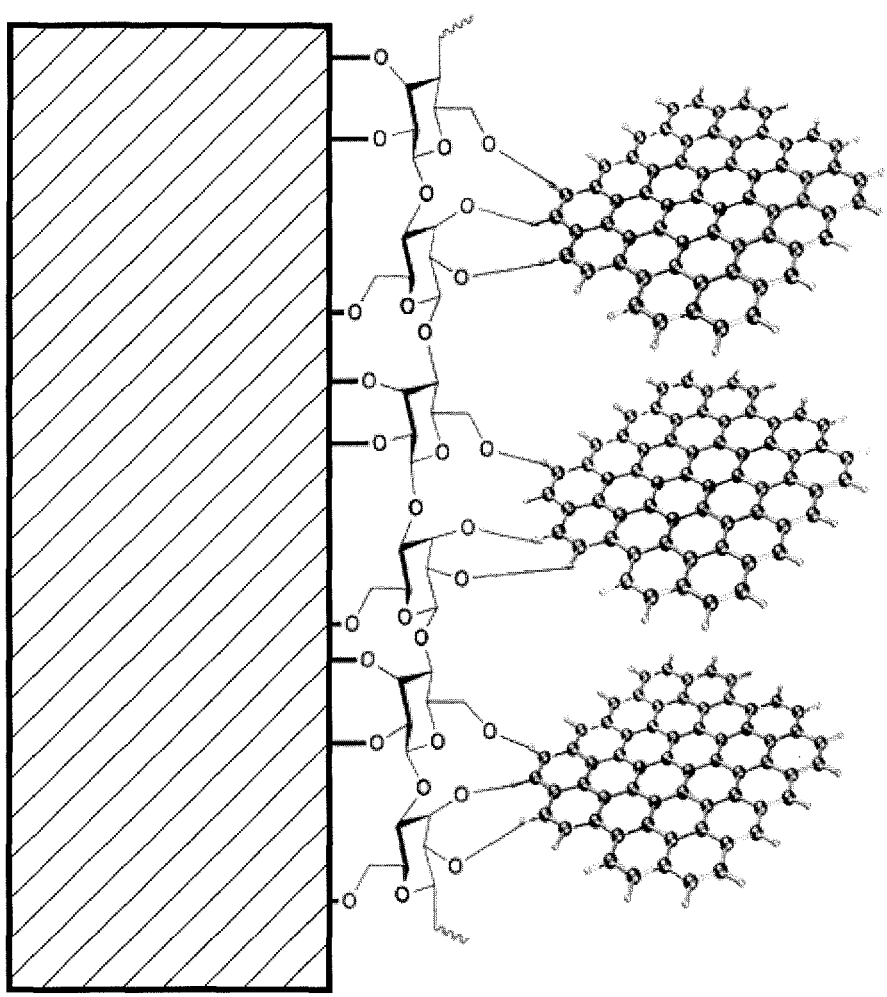
FIG. 2(B) is a schematic drawing of a portion of an exemplary fabric phase sorptive extractor (FPSE), using an insoluble graphene nanoparticle immobilized into sol-gel network covalently bonded to the fabric substrate, according to an embodiment of the invention.
Figure 3:
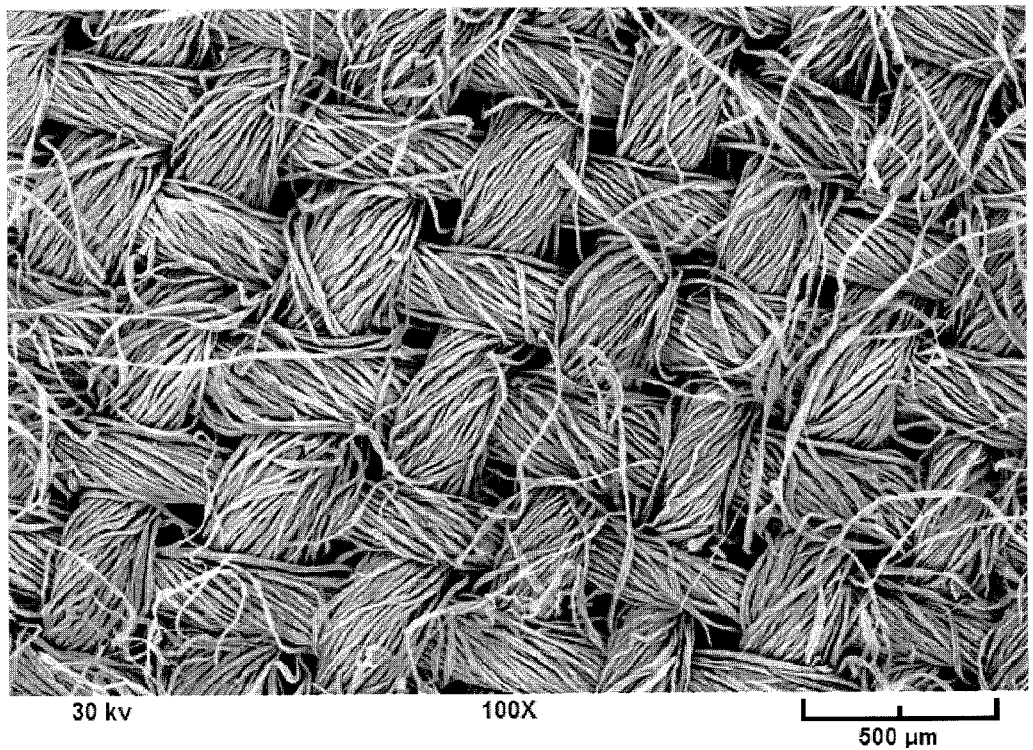
FIG. 3 is a Scanning Electron Microscopy (SEM) image of the surface of uncoated 100% cotton fabric phase sorptive extractor (FPSE) substrate, according to an embodiment of the invention.
Figure 4:
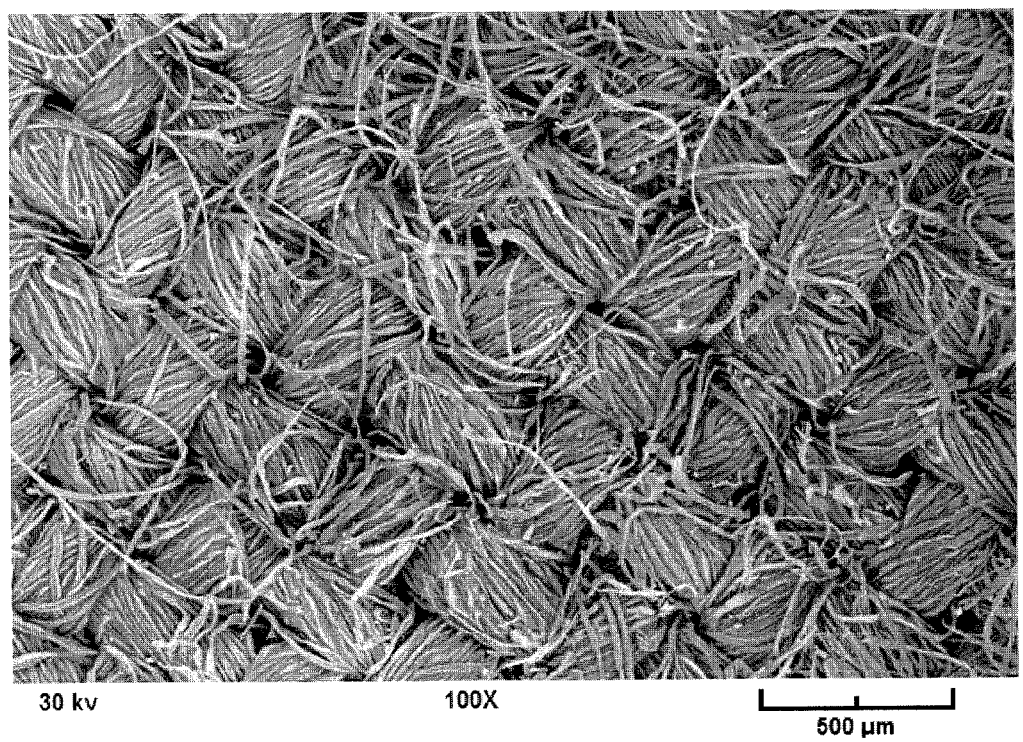
FIG. 4 is a Scanning Electron Microscopy (SEM) image of the surface of 100% cotton fabric phase sorptive extractor (FPSE) coated with thin sol-gel coating, according to an embodiment of the invention.
Figure 5:
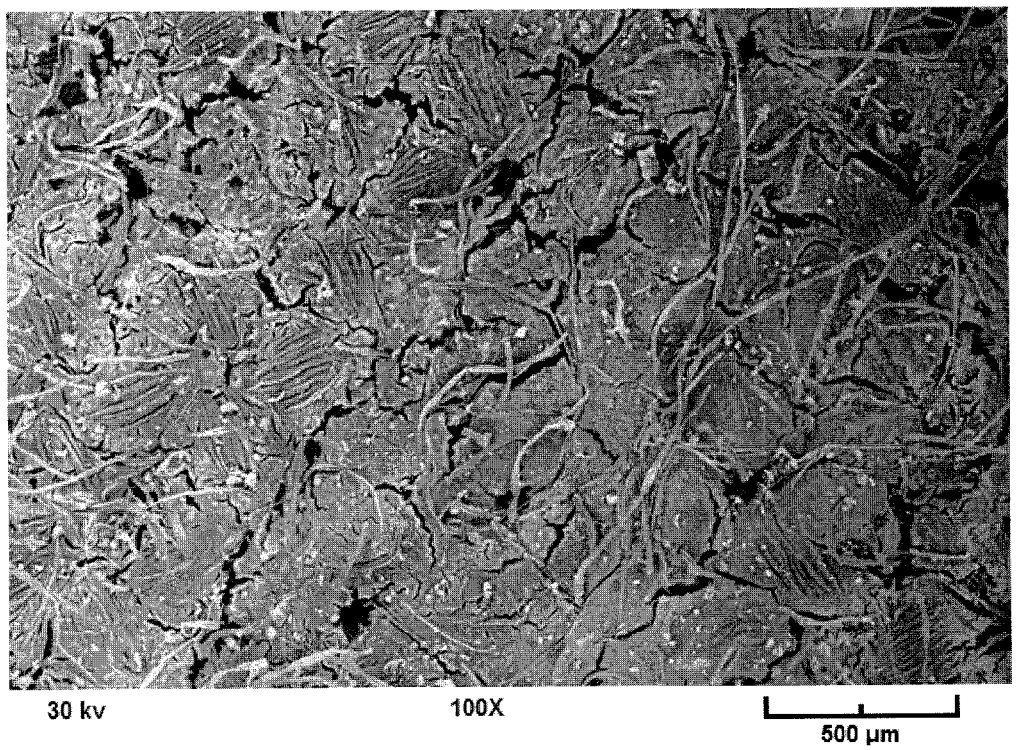
FIG. 5 is a Scanning Electron Microscopy (SEM) image of the surface of 100% cotton fabric phase sorptive extractor (FPSE) substrate coated with a thick yet flexible coating, according to an embodiment of the invention.
Figure 6:
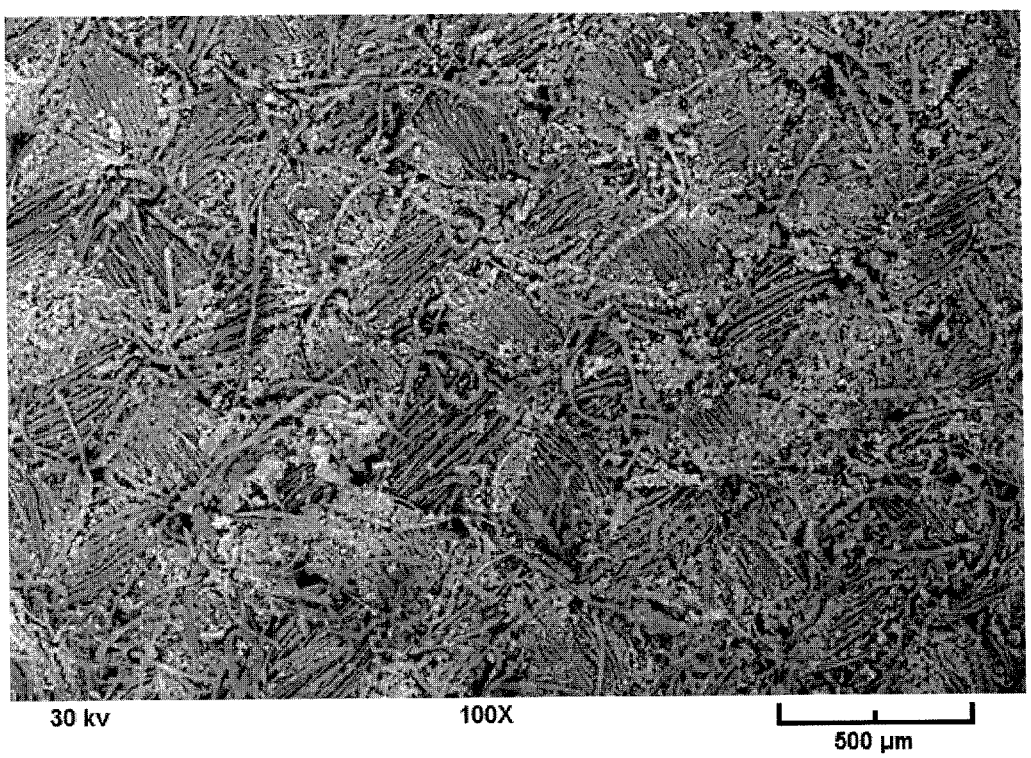
FIG. 6 is a Scanning Electron Microscopy (SEM) image of the surface of 100% cotton fabric phase sorptive extractor (FPSE) substrate coated with insoluble nanoparticles (Graphene) chemically immobilized using sol-gel process, according to an embodiment of the invention.

Embodiments of the invention are directed to fabric phase sorptive extractors (FPSE), where a flexible fabric sheet is surface modified with a conformal or quasi-conformal sol-gel film on the fabric that retains a high percentage of or even exceeds the fabric's surface area with the retention of the flexibility of the fabric. FIGS. 1 and 2 illustrate portions of fabrics with conformal sol-gel films. In this manner, the size of the FPSE sheet can be of a variety of sizes and the sol-gel sorbent film can be prepared to target a particular analyte or a plurality of analytes. The sol-gel sorbent film has constituents for bonding to the surfaces of the fabric, providing desired material properties, and promoting the binding of analytes for release upon exposure to materials or conditions that promote the release. The FPSE sheet can be extended during an analyte absorption process, and rolled or otherwise placed in a convenient geometry for storage, transport, and/or performance of an analyte removal step. The FPSE sheet permits extraction and subsequent removal of an analyte as a solution of a reasonable concentration for introduction to an inlet of an analytical instrument such as a gas chromatograph (GC), liquid chromatograph (LC), ion mobility spectrometer (IMS), capillary electrophoresis (CE), mass-spectrometer (MS) or other analytical instrument.

Fabrics that can be used, according to embodiments of the invention, include those comprising natural fibers, such as, but not limited to, cotton, other cellulose fibers, silk, wool, and other keratin fibers, and synthetic fibers, such as, but not limited to, polyesters, glass fiber, polyamides, acrylics, polyethylene, polypropylene, polyvinylidene fluoride, polyacrylonitrile, cellulose acetate or any other synthetic polymer that can be spun/cast into fibers that can be combined into flexible fabrics. The fabric is generally a thin sheet that is knitted or woven or cast and cut or otherwise formed into sheets that are of any desired shape, which is the unfolded shape of the ultimate FPSE. The two-dimensional shape of the sheet may be defined by an implement for positioning the FPSE in a sampling environment, or to fit in a device for removing the absorbed analytes. The fabric, can be stiff, but in general, the fabric can conform to many different shapes to permit sampling of various gaseous, liquid, or solid environments, where the FPSE can conform to a surface and, as desired, be rolled or otherwise consolidated into a container that is used during the removal of the analytes.

A sol-gel process is one where a sol, comprising at least one liquid or soluble precursor having a plurality of reactive substituents, is activated for hydrolysis or other nucleophilic reaction that transforms the reactive precursor substituents into reactive intermediate substituents, which subsequently undergo condensation reactions with other intermediate substituents or precursor substituents in the sol, ultimately forming an amorphous gel network. In embodiments of the invention, the gelation occurs on the surface of the flexible fabric to form a film that conforms to the surface of the fabric to a high degree, although, in many cases, some features of the fabric surface may be entirely obscured by the gel film; hence the film is generally quasi-conformal, where the surface of the gel only approximately reflects the surface features of the fabric surface to the extent that it is distinguishable from the fabric surface, and may be of lesser, equal, or greater surface area that that of the fabric surface. In embodiments of the invention, the sol includes precursor substituents that react with a surface functionality of the fabric to covalently bond the fabric to the gel film.

The sol can comprise precursors to gels of silica, titania, alumina, zirconia, germania, barium oxide, gallium oxide, indium oxide, thallium oxide, vanadium oxide, cobalt oxide, nickel oxide, chromium oxide, copper oxide, iron oxide, lanthanum oxide, niobium oxide, zinc oxide, boron oxide, or any combination thereof. For the purposes of this invention, the precursors utilized for the sorbent coating have the general structure:

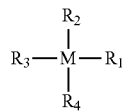

wherein, M is the precursor-forming element taken from any metal oxide, but not limited to, metal oxides listed above, $R_1$, $R_2$, $R_3$ and $R_4$ are substituents groups at least two of which are sol-gel active, wherein the sol-gel active groups include, but not limited to, alkoxy, hydroxy, halides, and dialkylamino. Remaining R groups may be non-sol-gel active and may include alkyl moieties and their derivatives, arylene moieties and their derivatives, cyanoalkyl moieties and their derivatives, fluoroalkyl moieties and their derivatives, phenyl moieties and their derivatives, cyanophenyl moieties and their derivatives, biphenyl moieties and their derivatives, cyanobiphenyl moieties and their derivatives, dicyanobiphenyl moieties and their derivatives, cyclodextrin moieties and their derivatives, crown ether moieties and their derivatives, cryptand moieties and their derivatives, calixarene moieties and their derivatives, dendrimer moieties and their derivatives, graphene moieties and their derivatives, carbon nanotubes and their derivatives, chiral moieties and other similar non-sol-gel active moieties.

The silica precursor can be any reactive silane compatible with any solvent of the sol and other components of the sol. For example, the silane can be a tetraalkoxysilane, tetraacetoxysilane, tetrachlorosilane, tetradialkylaminosilane or any other silica precursor. For example, tetramethoxysilane or tetraethoxysilane can be used as a silica precursor. In like manner, a tetraalkoxytitanate can be used as a titania precursor, trialkoxyaluminum can be used as an alumina precursor, and other metal alkoxides can be the source of zirconia, germania, gallium oxide, indium oxide, thallium oxide, vanadium oxide, cobalt oxide, nickel oxide, chromium oxide, copper oxide, iron oxide, lanthanum oxide, niobium oxide, zinc oxide, boron oxide, or barium oxide incorporated into the ultimate gel of the FPSE. Generally, but not necessarily, the alkoxy and dialkylamino groups are $C_1$ to $C_4$ alkoxy and dialkylamino groups.

The sol can further comprise one or more siloxy precursors to the gel that reside as monoalkylsiloxy, monoarylsiloxy, dialkylsiloxy, diarylsiloxy, or any combination of these precursors to a gel, where the alkyl or aryl groups can be unsubstituted, or substituted with functional groups for modification of the properties of the gel, to promote a specific affinity for one or more analytes, to react with other components included in the sol, and/or to have an affinity for a fabric surface. Hence, the siloxy precursor can be, but is not limited to, a trialkoxyalkylsilane, trialkoxyarylsilane, dialkoxydialkylsilane, alkoxyalkylarylsilane, dialkoxydiarylsilane, triacetoxyalkylsilane, triacetoxyarylsilane, diacetoxydialkylsilane, diacetoxyalkylarylsilane, diacetoxydiarylsilane, trichloroalkylsilane, trichloroarylsilane, dichlorodialkylsilane, chloroalkylarylsilane, dichlorodiarylsilane, tridialkyaminoalkylsilane, tri(dialkyamino)arylsilane, di(dialkyamino)dialkylsilane, di(dialkyamino)alkylarylsilane, di(dialkyamino)diarylsilane, or any combination thereof. The alkoxy and dialkylamino groups are generally, but not necessarily, $C_1$ to $C_4$ alkoxy and dialkylamino groups. The alkyl groups are generally, but not necessarily, $C_1$ to $C_4$ groups and aryl groups are generally, but not necessarily phenyl groups. The alkyl and/or phenyl groups can be substituted with a functional group, such as, but not limited to amino, hydroxyl, carboxylic acid, acid anhydride, epoxy, acrylate, methacrylate, and vinyl. The siloxane precursor can be an oligo or polysiloxane that comprises: dialkylsiloxanes; alkylarylsiloxanes; diarylsilanes; alkylhydrogensiloxanes; or any combination thereof. The alky groups include, but are not limited to, methyl, ethyl, n-propyl, isopropyl, n-butyl, sec-butyl, and tert-butyl groups. The aryl groups are generally, but not necessarily, phenyl groups. The oligo and polysiloxanes comprise at least one reactive group, which can be on one or both terminal units, for example an α,ω-dihydroxypolydimethylsiloxane, or can reside on a silicon, alkyl, or aryl group of a repeating unit. Other reactive groups, in addition to hydroxy groups, that can reside on terminal or internal silicon atoms of repeating units include, but not limited to, acetoxy, hydrogen, chloro, dialkylamino, and γ-aminopropyl.

The sol can further comprise one or more organic precursors that have functionality that is reactive with the precursor substituents, reactive intermediate substituents, or with the functionality on the siloxy precursors. The organic precursors can be monomeric, oligomeric, or polymeric, where there is at least one functionality on the organic precursor that can react with a reactive precursor substituent, a reactive intermediate substituent, or a reactive functionality of a siloxy precursor in the sol. When the organic precursor has a plurality of functionalities, the organic precursor can react with the functionality of another organic precursor in addition to reacting with a functionality of the sol or the gel that is not of the organic precursor. The organic precursor can have additional functionality for modifying the properties of the gel, functionality that provides an affinity for a target analyte, or functionality that provides an affinity for the surface of the fabric. Polymeric organic precursors can be homopolymers or copolymers, and can have a linear, branched, star-branched, hyper-branched, or dendritic structure. The organic precursors, and functional groups on the siloxy precursors, can be reactive functionality that do not involve hydrolysis and can be functionality that undergo addition or polyaddition reactions rather than condensation reactions to be incorporated into the gel. Organic precursors include, but are not limited to, α,ω-dihydroxyalkanes, α,ω-dihydroxy-poly(ethylene oxide), α,ω-dihydroxy-polypropylene oxide, α,ω-dihydroxy-poly(ethylene oxide-co-propylene oxide), α,ω-dihydroxy-poly(butylene oxide), α,ω-dihydroxy-polyamides, and α,ω-dihydroxy-polyesters. Polymers can be of low degree of polymerization and may be oligomers. The organic precursor can include monomers, oligomers, and/or polymers with pendant reactive functionality, for example, but not limited to, a partially hydroxylated polybutadiene. In addition to hydroxy groups, the reactive groups can be complementary reactive functionality to reactive groups of the siloxane precursors, and can be, but are not limited to, amino, hydroxyl, carboxylic acid, acid anhydride, epoxy, acrylate, methacrylate, and vinyl. Monomeric organic precursors include, but are not limited to, divinylbenzene. Oligomeric organic precursors include, but are not limited to, $\alpha,\omega$-diacrylates of oligoesters. Polymeric organic precursors can be homopolymers, random copolymers, alternating copolymers, block copolymers, or graft-copolymers, and can be linear, branched, hyper-branched, star, or dendritic.

Functionality that provide specific affinity for analytes can include those which provide specific interactions, such as ionic functionalities, ion complexing functionalities, hydrogen bonding, plurally hydrogen bonding functionality, $\pi$-stacking functionality, or any other functionality that augments the van der Waals, dipole, induced dipole or other inherent intermolecular forces displayed between the gel and analyte. Functionality that provide specific affinity for analytes include, but are not limited to, bidentate ligands, polydentate ligands, crown ethers, cryptands, aryenes, graphene, fullerenes, hydroxyfullerenes, cyclodextrin, calixarene, and carbon nanotubes. Functionality that provides specific affinity for an analyte can be enantiomeric and not a racemic mixture for chiral selectivity of an analyte.

Figure 7:
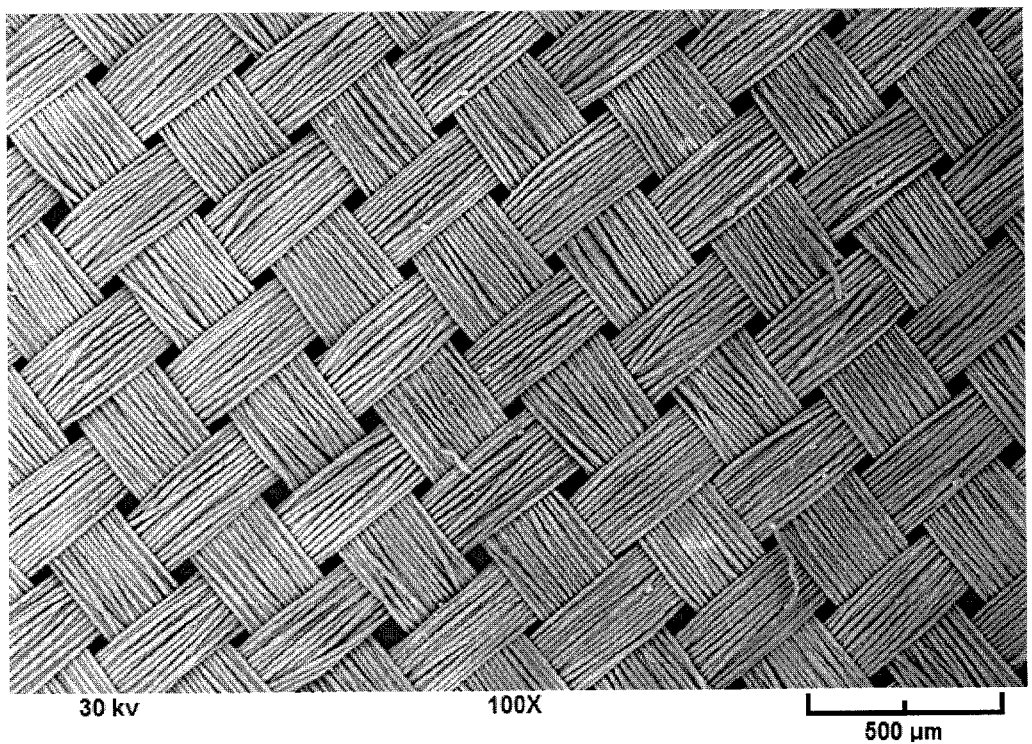
FIG. 7 is a Scanning Electron Microscopy (SEM) image of the surface of uncoated 100% polyester fabric phase sorptive extractor (FPSE) substrate, according to an embodiment of the invention.
Figure 8:
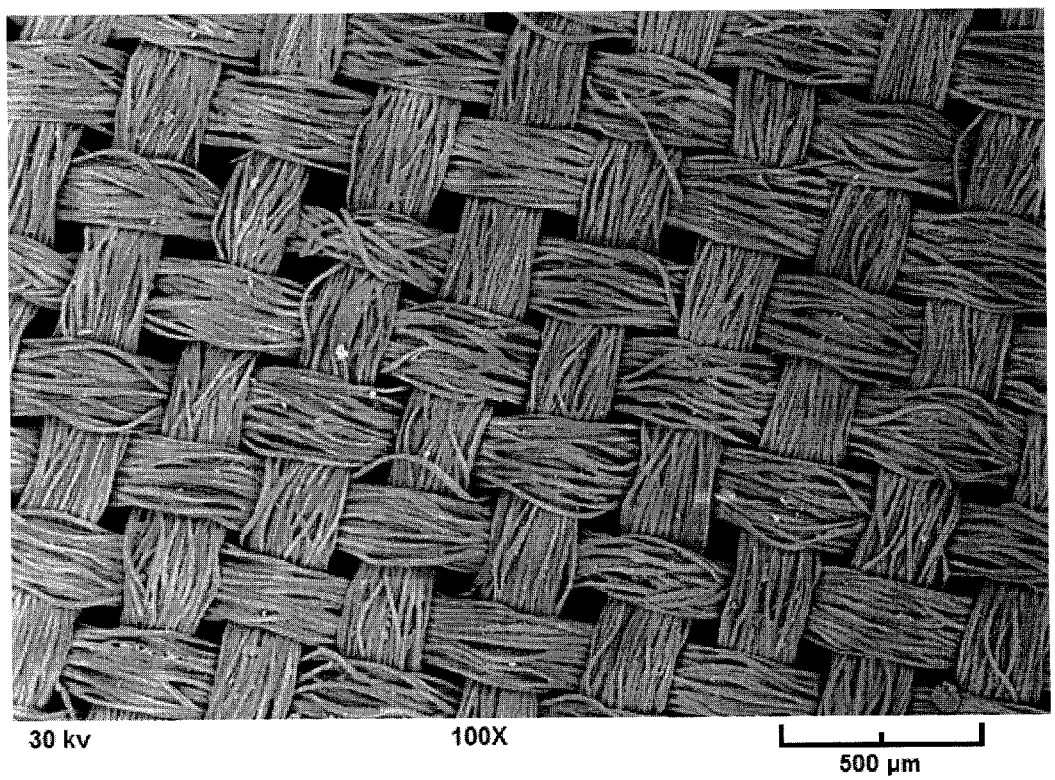
FIG. 8 is a Scanning Electron Microscopy (SEM) image of the surface of 100% polyester fabric phase sorptive extractor (FPSE) substrate coated with thin sol-gel coating, according to an embodiment of the invention.
Figure 9:
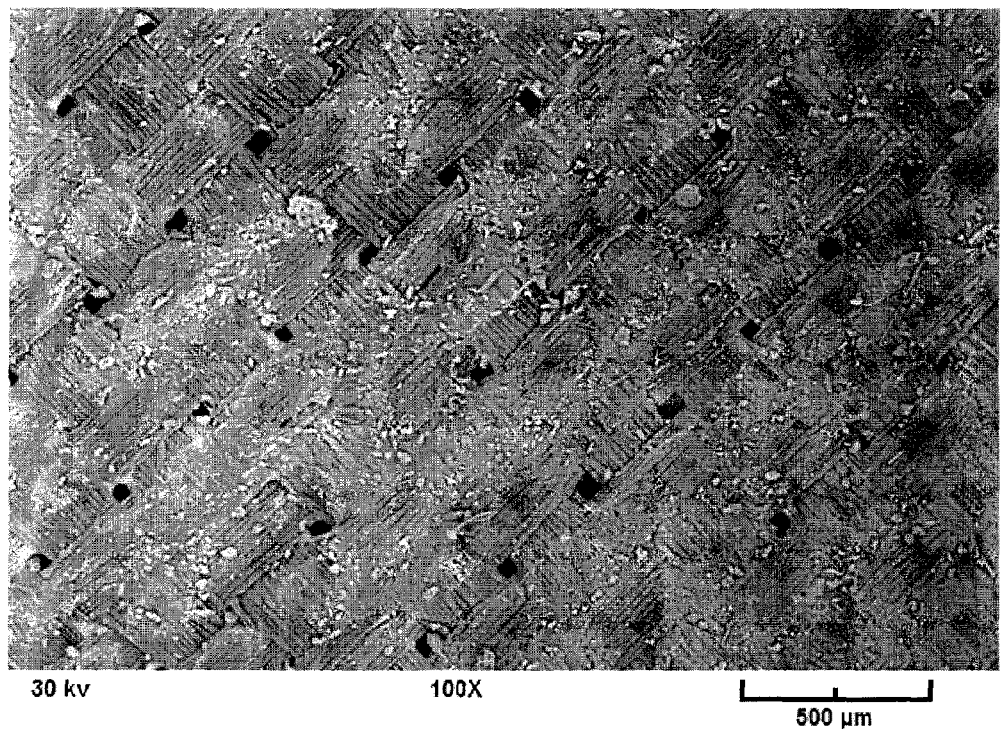
FIG. 9 is a Scanning Electron Microscopy (SEM) image of the surface of 100% polyester fabric phase sorptive extractor (FPSE) substrate coated with a thick yet flexible coating, according to an embodiment of the invention.

The sol-gel process is carried out in the presence of the fabric and can be carried out in a single physical step, for example, contacting the fabric with a sol solution comprising all pre-gel precursors. The sol-gel process can be carried out in a plurality of physical steps where a portion of the pre-gel precursors are in the initial fabric contacting solution, and after a desired degree of reaction has occurred in that step, additional gel precursors as neat liquids or as solution are added to the fabric contacting solution. In this manner, the gelation can occur by a sequence of reactions that would not occur in a single mixture of all sol precursors. As necessary, the first step of the sol-gel process can be a modification of the fabric surface by chemically reacting with the surface, or by depositing a gel precursor that has a strong physical affinity for the fabric surface and is not readily disrupted by subsequent gelation steps or upon use of the ultimate FPSE. The surface of uncoated fabrics and the surface after carrying out the sol-gel process on the surface are illustrated in FIGS. 3 through 6 for a cotton fabric and FIGS. 7 through 9 for a polyester fabric.

In addition to the sol-gel precursors, the sol can include one or more agents that promote, initiate, or catalyze reactions to form the gel. For example, acids, bases, or radical initiators can be included. The sol can include agents that are porogens for producing pores, foaming agents, and templates for forming binding sites that bind specific analytes that are absorbed in a specifically shaped and functionalized cavity. For example, the template can form a binding site similar to that found in enzymes and with other biopolymers, such as other proteins and nucleotides. The template can be the analyte or a mimic of the analyte. Indicators can be included in the sols and ultimately in the gel, such that the environment in which the FPSE is employed for extraction of an analyte is reflected. For example, colorimetric indicators can change in color based on the pH or oxidative environment of the target environment, such that these factors and their environment's consequences on the efficiency of the FPSE to absorb the target analytes can be anticipated by technicians at some point before analysis of an extracted sample is completed.

The FPSE can include a mono film of the absorbent gel or it can include a plurality of films overlaying the fabric, where the films are incapable of delamination from the fabric or an adjacent film. The plurality of films can be of like composition. The plurality of films can be of different composition, such that the affinity of one analyte is great for one film and lesser in another that has a strong affinity for a different analyte. The first deposited of a plurality of films may be a film that is deposited for bonding or binding to the fabric surface and is not necessarily contributing to the absorption of any analyte.

The absorbent gel can be deposited on the fabric by dip coating, roll coating, spray coating, spin coating, painting, electrodeposition, or any other method to contact the fabric and the sol. In an embodiment of the invention, different portions of the fabric can be coated with gels with affinities to different analytes. For example, different sols can be deposited in different portions of a fabric by ink-jet printing or other methods that specifically address a specific portion of the fabric. The fabric can be coated in a continuous manner while being transferred from one spool to another, where the fabric is drawn through, underneath, or between one or more baths, rollers or sprayers. As desired the gel coated fabric can be heated or irradiated in any batch or continuous preparation of the FPSE. When deposition and cure of the gel is complete, the FPSE can be washed with one or more appropriate solvents, which can be a mixture or used sequentially, to remove unreacted precursors, deposition solvents, or side products, for example, cyclosiloxane or polymers capped with unreacted or incompletely reacted precursors. Additionally or alternatively, the prepared FPSE can be heated and/or evacuated to remove volatiles. Generally, but not necessarily, a solvent that is used for one or more washings is any solvent that is of the environment for testing, for example, water. The final FPSE can be formed by cutting the continuous gel-coated fabric sheet into smaller FPSE sheets of the desired shape and size. The shape can be a square, rectangle, triangle, circle, oval, or any other shape suited for the sampling and/or any subsequent analyte removal protocol. The size of the FPSE can be any reasonable size, such as a square of 5 cm, a rectangle of 2.5×4 cm, a circle of 10 mm diameter, a circle of 47 mm, or any other size where the longest dimension is less than about 20 cm. The fabric can be cut before deposition of the sol.

Figure 10:
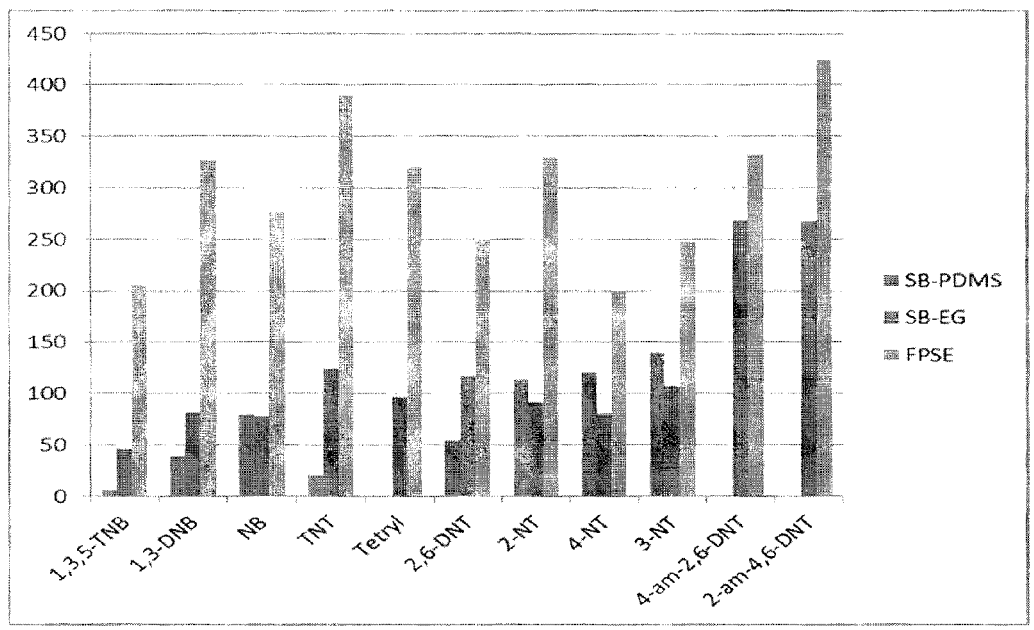
FIG. 10 is a bar graph that compares the relative extraction efficiencies of a commercially available GERSTEL TWISTER® (PDMS Stir bar, SB-PDMS), a GERSTEL® EG/Silicone (Ethylene glycol-silicone, SB-EG), and a FPSE of 5 cm$^2$, according to an embodiment of the invention, under identical extraction condition.

According to an embodiment of the invention, the FPSE is employed in a method of sampling for a target analyte. The analyte can be any compound whose presence at a location is indicative of one with biological, environmental, food, pharmaceutical, bio-analytical, clinical, forensic, toxicological, national security, public health, and/or safety implications. The nature and structure of the gel is selected for analysis of one of more target analytes. The nature and structure of the fabric is chosen to be appropriate to allow deposition of the sol and formation of the selected gel. A portion of exemplary FPSEs, according to an embodiment of the invention, which can be used with a wide variety of analytes, is shown in FIGS. 1 and 2. The exemplary FPSE is a flexible cellulose comprising fabric coated with a gel coating that is prepared from methyltrimethoxysilane and $\alpha,\omega$-dihydroxy-poly(tetrahydrofuran). The extraction efficiencies of FPSEs are superior to commercially available devices, as shown in FIG. 10. The reproducibility of the extraction by equivalent FPSEs is shown in FIGS. 11 and 12. The resiliency of the FPSEs for extraction after exposure to varying environments is illustrated in FIG. 13.

Figures 13, 14:
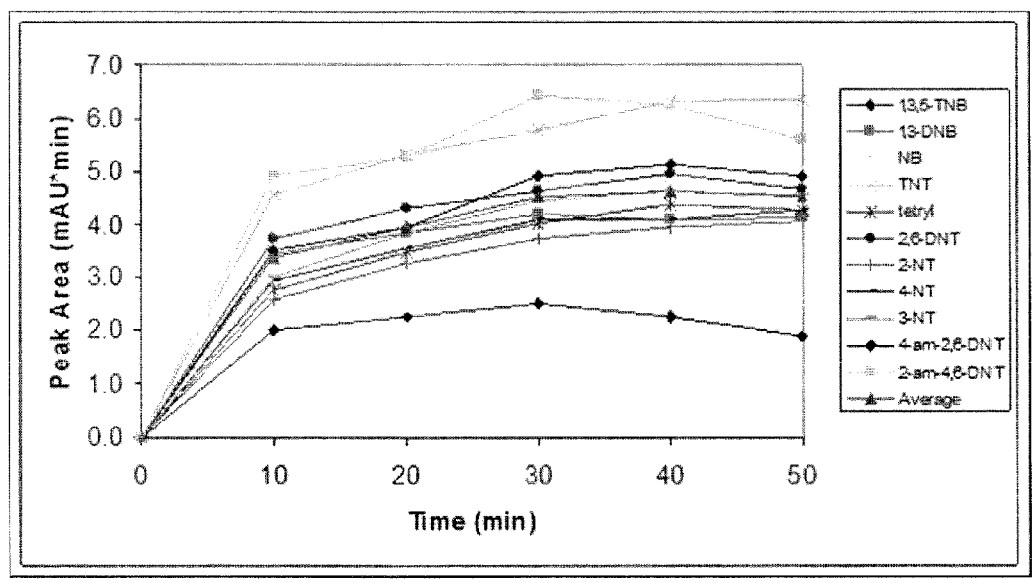
FIG. 13 is a table showing the resiliency of a FPSE's extraction capability, according to an embodiment of the invention, to various treatment protocols where the FPSE is exposed to: organic solvent, acidic solution, and basic solution, where extraction efficiency is not adversely affected.
FIG. 14 is a plot of the analyte quantities sampled under equilibrium extraction conditions from aqueous solutions by an FPSE, according to an embodiment of the invention.
Figure 15:
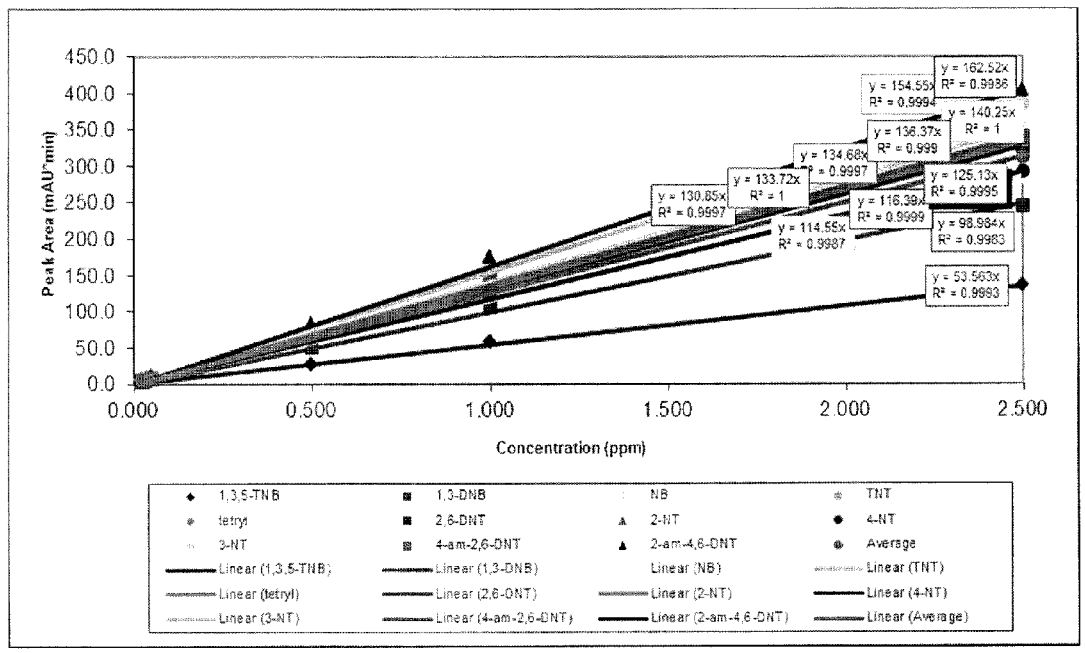
FIG. 15 is linear plot over three orders of magnitudes for exhaustive extraction by a FPSE, according to an embodiment of the invention, of explosives from aqueous solution.
Figure 16:
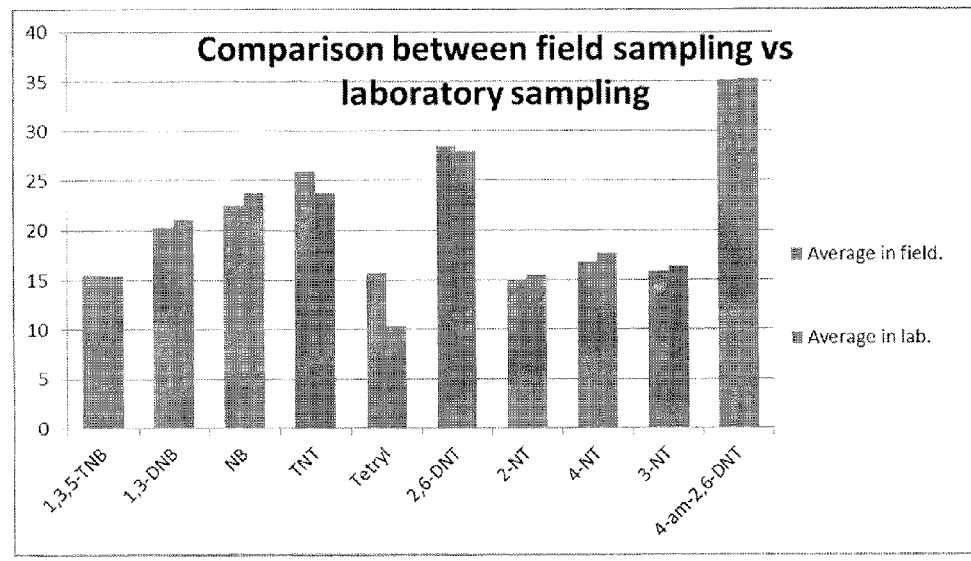
FIG. 16 is a bar graph that compares the extraction efficiencies of field and laboratory sampling using an FPSE, according to an embodiment of the invention where extraction and solvent desorption were carried out in situ in the field or in the laboratory under otherwise identical conditions.
Figure 17:
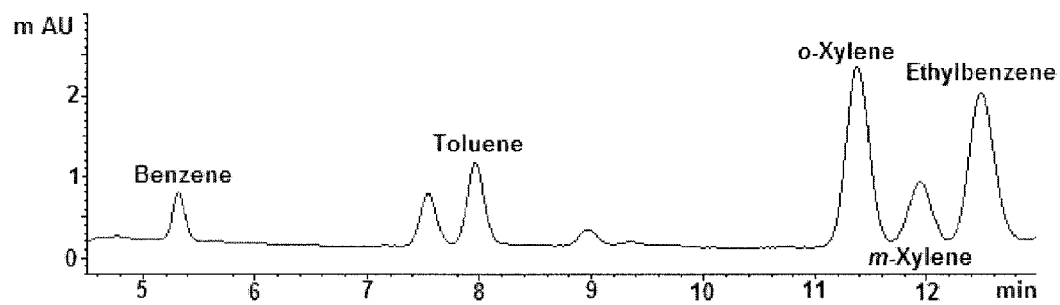
FIG. 17 is a chromatogram of fabric phase sorptive extracted BTEX (benzene, toluene, ethyl benzene, and xylenes) from environmental samples, according to an embodiment of the invention.
Figure 18:
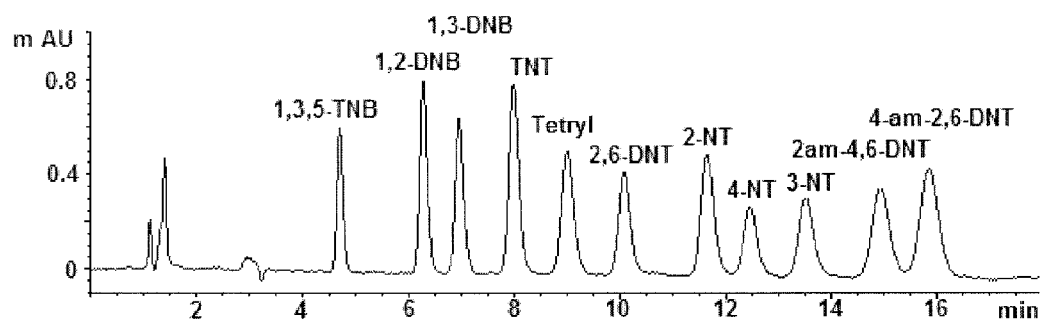
FIG. 18 is a chromatogram of fabric phase sorptive extracted high explosives (HE) from environmental samples, according to an embodiment of the invention.
Figure 19:
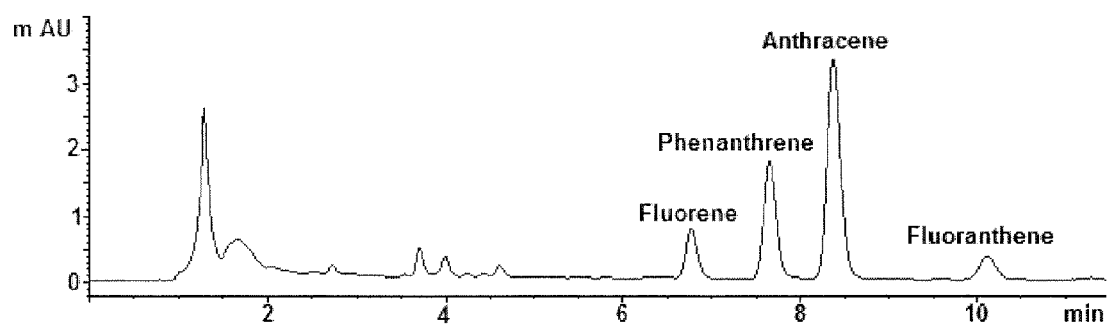
FIG. 19 is a chromatogram of fabric phase sorptive extracted polycyclic aromatic hydrocarbons (PAHs) from environmental samples, according to an embodiment of the invention.
Figure 20:
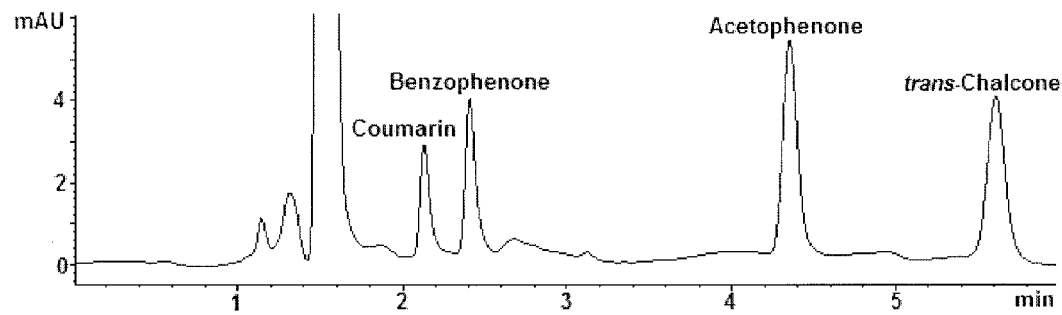
FIG. 20 is a chromatogram of fabric phase sorptive extracted ketones from environmental samples, according to an embodiment of the invention.
Figure 21:
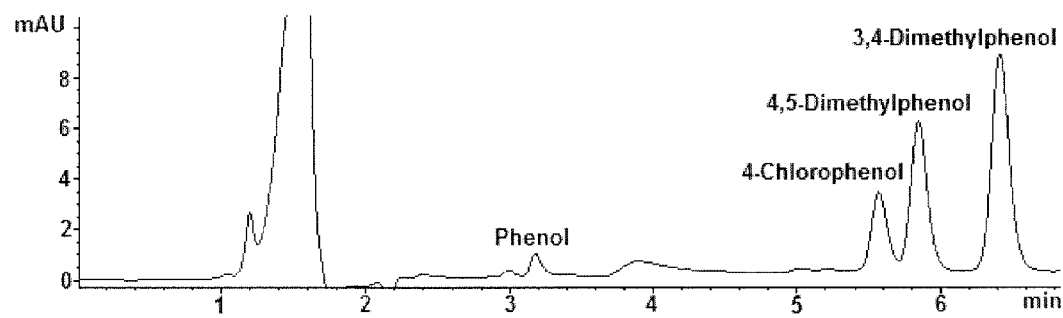
FIG. 21 is a chromatogram of fabric phase sorptive extracted phenols from environmental samples, according to an embodiment of the invention.
Figure 22:
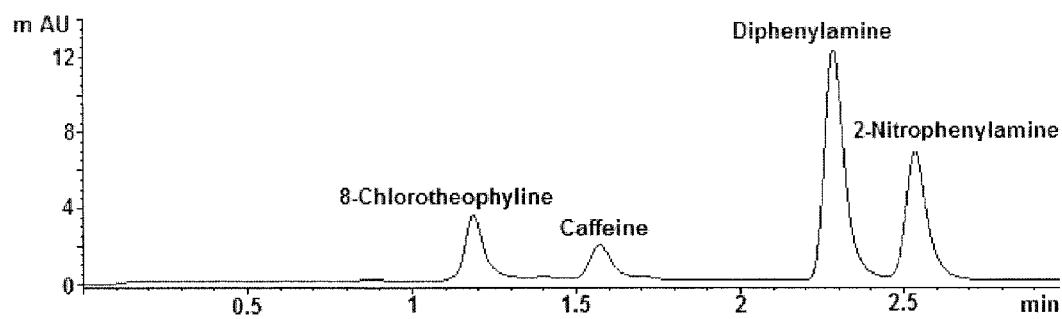
FIG. 22 is a chromatogram of fabric phase sorptive extracted amines from environmental samples, according to an embodiment of the invention.
Figure 23:
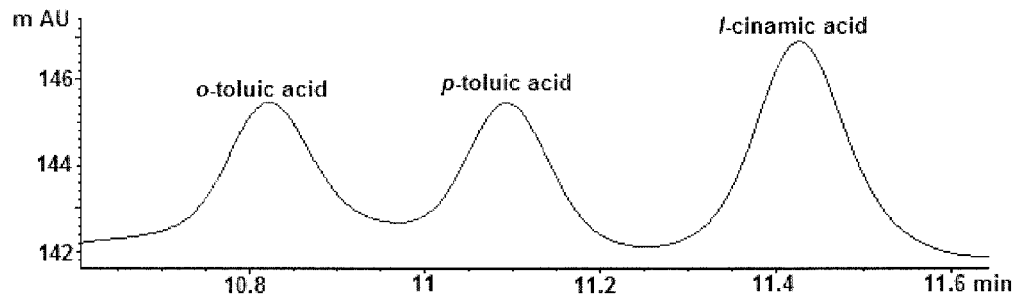
FIG. 23 is a chromatogram of fabric phase sorptive extracted organic acids without derivatization from aqueous samples, according to an embodiment of the invention.

Although the FPSEs, according to embodiments of the invention, are well suited for equilibrium based extractions, as illustrated by the plot of analyte extracted over time in FIG. 14, where the analyte is partitioned between the FPSE and the environment in which the analyte is suspected, some FPSEs can be used for exhaustive extraction, as illustrated in FIG. 15. Where the affinity of the FPSE is extremely high relative to that of the environment, for example, when the analyte is a relatively non-polar compound in a water environment, a known volume of the water solution can be passed through the FPSE, or the FPSE can be suspended in the water solution, permitting the analyte to be exhaustively absorbed on the FPSE. The FPSE can be calibrated, individually or for a manufactured lot, by partitioning a target analyte of known concentration in known volume of an artificial environment to determine the partition coefficient of the target analyte under those conditions. A calibration can be provided with a FPSE. According to an embodiment of the invention, the FPSE, which had been placed for a desired period in the testing environment that was suspected of containing the target analyte, is used for providing an analytical sample removed from the FPSE. As shown in FIG. 16, sample acquired in a field sampling and transported for analysis are comparable to that where the sample is brought to the laboratory. When the sampled suspect environment decorates the FPSE with unwanted solid particulates, the particulates can be removed, as needed, by impinging the surface with a clean air, nitrogen, or other gas stream to release and entrain the particulates from the surface of the FPSE. The FPSE can be used for sampling water collected from a pond or other body of water that contains a high volume of particulates and debris, allowing a direct extraction of target analytes without the sampled water's pretreatment such as filtration, sedimentation, or centrifugation. In one embodiment of the invention, the FPSE is placed in a removal container and combined with a solvent or solution known to remove preferentially the target analyte from the FPSE. The FPSE can be placed in the removal container in a prescribed fashion that can include rolling, folding, cutting, or any other needed manner, where the removal container is of a desired volume and geometry to achieve the desired removing conditions. In an embodiment of the invention, a removal container is provided with a FPSE such that the FPSE can be immediately inserted into the container after sampling at the suspect environment site. An individual FPSE can be calibrated for this partitioning process prior to its use such that upon combination of a FPSE with a known quantity of an analyte removing solvent or solution, the amount removed can be correlated to the amount absorbed by the FPSE that had been placed in the suspect environment.

In another embodiment of the invention, the target analyte can be removed as a volatile, where the FPSE is suspected of containing the target analyte by placing the FPSE in a removal container that is heated and/or evacuated at a prescribed temperature and pressure for a prescribed duration where the removal contain is in fluid communication with a volatiles trap where the target analytes are condensed. The condensed target analytes are dissolved in a solvent to form a target analyte solution, or the volatiles trap is inserted or otherwise connected to an inlet port of an analytical instrument. The FPSE can be placed in the container in a prescribed fashion that can include rolling, folding, cutting, or any other needed manner, where the container is of a desired volume and geometry to achieve the desired removing conditions. In an embodiment of the invention, the container is provided with the FPSE such that the FPSE can be immediately inserted into the container after the sampling process is completed in the suspect environment. In an embodiment of the invention, the devolatilization of the target analyte from the FPSE is carried out in a unit for desorption, for example, thermal desorption, that is a portion of or connected to the inlet of an analytical device.

Figure 24:
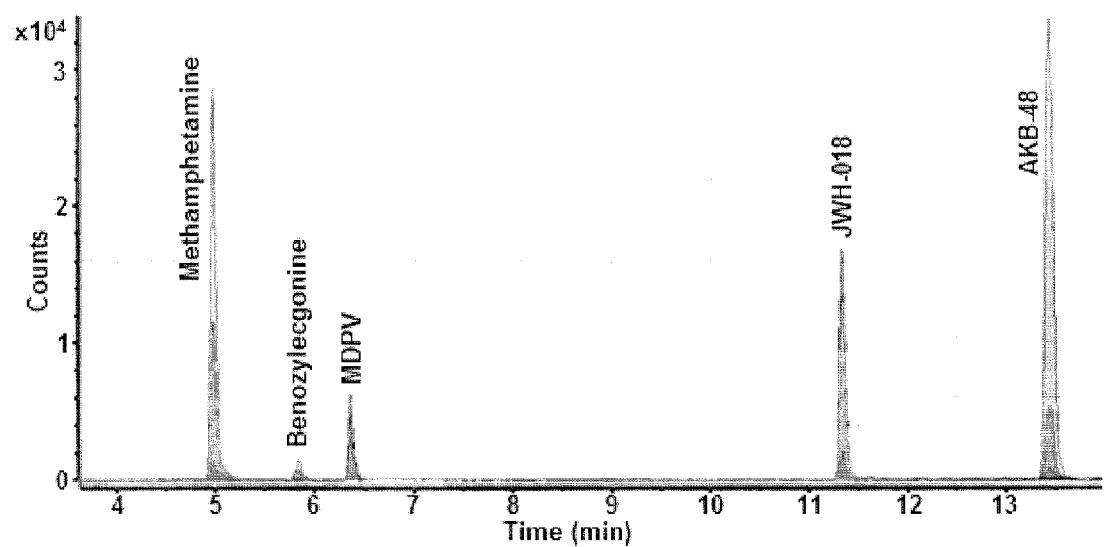
FIG. 24 is a chromatogram of fabric phase sorptive extracted 20 ppb illicit drugs in a in blood sample, according to an embodiment of the invention

The sample released from the FPSE can be analyzed for a target analyte. The analysis can be carried out by any known method that is appropriate for the target analyte. For example, GC, LC, IMS, capillary electrophoresis, mass spectrometry, or any other method can be employed with the sample removed from the FPSE. FIGS. 17-23 show chromatographic traces for various analyzed environmental samples that were collected employing FPSEs. FIG. 24 shows a chromatographic trace of a blood sample containing illicit drugs that was extracted using a FPSE.

The FPSE enable a wide variety of sampling environments. For example, the FPSE can be used as a sampling device that is suspended in a gas or a liquid. For example, the FPSE can be fastened to a holder to permit a flow of a gas or liquid around and/or through the surfaces of the FPSE. For example, the FPSE can be placed on a wet or dry surface such that the FPSE contacts as much of the surface as possible. For example, the FPSE can be used as a wipe, where a small volume of liquid or an apparently dry surface is wiped by the FPSE. In this manner, one or more FPSEs can be carried by an inspector, enforcement officer, testing technician, or any other individual to an environment suspected of having a particular target analyte, or an environment where assurance is needed that the target analyte is present or assurance is needed that the target analyte is absent. One or more FPSEs are useful for sample collection and subsequently isolation of natural or synthetic organic or inorganic compounds, salts, ions, or biological molecules. One or more FPSEs can be used for specific and general monitoring of target analytes in the natural environment, at chemical and pharmaceutical processing plants, at food processing plants, at crime scenes, at sites of interest for national security, at sites monitored for public health and safety, at power generation stations, at medical facilities, with patients, and in any other environment where a convenient, rapid and reproducible sampling is desired.

It should be understood that the examples and embodiments described herein are for illustrative purposes only and that various modifications or changes in light thereof will be suggested to persons skilled in the art and are to be included within the spirit and purview of this application.

We claim:

1. A fabric phase sorptive extractor (FPSE), comprising:
    a flexible fabric;
    a binding gel film, wherein the binding gel film is bound or bonded to the flexible fabric and wherein the binding gel film comprises a first metal oxide portion, and/or a first siloxy portion, and/or a first organic portion;
    a first absorbent gel film bound to the binding gel film, wherein the first absorbent gel film comprises at least two of: a second metal oxide portion; a second siloxy portion; and a second organic portion, wherein the second siloxy portion and/or the second organic portion is polymeric, wherein at least a portion of the first absorbent gel film is amorphous, wherein the first absorbent gel film is absorbent toward at least one target analyte; and
    optionally, at least one second absorbent gel film bound to the binding gel film or the first absorbent gel film or one of the at least one second absorbent film, wherein the second absorbent gel film comprises at least two of: a second metal oxide portion; a second siloxy portion; and a second organic portion, wherein the second siloxy portion and/or the second organic portion is polymeric, wherein at least a portion of the first absorbent gel film is amorphous, wherein the second absorbent gel film is absorbent toward at least one target analyte and wherein the FPSE is flexible.

2. The FPSE of claim 1, wherein the flexible fabric is cotton, cellulose, silk, wool, glass fiber, polyesters, polyamides, polyacrylates, polymethacrylates, polyethylene, polypropylene, polyvinylidene fluoride, polyacrylonitrile, or cellulose acetate.

3. The FPSE of claim 1, wherein the flexible fabric is a woven or knitted fabric of threads or yarns comprising a plurality of fibers.

4. The FPSE of claim 1, wherein the second metal oxide portion is a silica, titania, alumina, zirconia, germania, barium oxide, gallium oxide, indium oxide, thallium oxide, vanadium oxide, cobalt oxide, nickel oxide, chromium oxide, copper oxide, iron oxide, lanthanum oxide, niobium oxide, zinc oxide, boron oxide, any combination thereof, or a substituted metal oxide from a precursor of the structure:

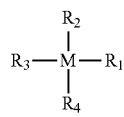

wherein: M is silicon, titanium, aluminum, zirconium, germanium, barium, gallium, indium, thallium, vanadium, cobalt, nickel, chromium, copper, iron, lanthanum, niobium, zinc, or boron; at least two of $R_1$, $R_2$, $R_3$ and $R_4$ are independently alkoxy, hydroxy, halides, hydrogen or dialkylamino, and remaining $R_1$, $R_2$, $R_3$ and $R_4$ are independently substituted or unsubstituted alkyl, aryl, cyanoalkyl, fluoroalkyl, phenyl, cyanophenyl, biphenyl, cyanobiphenyl, dicyanobiphenyl, cyclodextrin moieties, crown ether moieties, cryptand moieties, calixarene moieties, dendrimer moieties, graphene moieties, carbon nanotubes, or wherein the $R_1$, $R_2$, $R_3$ and $R_4$ is chiral or achiral.

5. The FPSE of claim 1, wherein the second siloxy portion can be formed from a hydrolysis and condensation of a trialkoxyalkylsilane, trialkoxyarylsilane, dialkoxydialkylsilane, alkoxyalkylarylsilane, dialkoxydiarylsilane, triacetoxyalkylsilane, triacetoxyarylsilane, diacetoxydialkylsilane, diacetoxyalkylarylsilane, diacetoxydiarylsilane, trichloroalkylsilane, trichloroarylsilane, dichlorodialkylsilane, chloroalkylarylsilane, dichlorodiarylsilane, tri(dialkyamino)alkylsilane, tri(dialkyamino)arylsilane, di(dialkyamino)dialkylsilane, di(dialkyamino)alkylarylsilane, di(dialkyamino)diarylsilane, or any combination thereof, wherein alkyl groups are $C_1$ to $C_4$ alkyl groups and aryl groups phenyl groups, alkyl substituted phenyl groups, or polycyclic aromatic groups, wherein the alkyl groups and phenyl groups are unsubstituted or independently substituted with amino, hydroxyl, carboxylic acid, acid anhydride, epoxy, acrylate, methacrylate, vinyl, or reaction residue therefrom.

6. The FPSE of claim 1, wherein the second organic portion is monomeric, oligomeric or polymeric.

7. The FPSE of claim 1, wherein the second organic portion comprises poly(ethylene oxide), polypropylene oxide, poly(ethylene oxide-co-propylene oxide), poly(butylene oxide), polyamide, polyester, or polybutadiene, where one or more carbons of the organic portion is unsubstituted or independently substituted with an amino, hydroxyl, carboxylic acid, acid anhydride, epoxy, acrylate, methacrylate, vinyl, or reaction residue therefrom.

8. The FPSE of claim 1, wherein the second siloxy portion and/or organic portion comprises at least one Si or C atom independently substituted with a bidentate ligand, polydentate ligand, crown ether, cryptand, aryene, graphene, fullerene, hydroxyfullerene, cyclodextrin, calixarene, or carbon nanotubes.

9. The FPSE of claim 1, wherein a surface of the first absorbent gel film or at least one of the at least one second absorbent gel film that is distal to the flexible fabric has a surface area greater than the flexible fabric's surface area.

10. The FPSE of claim 1, wherein the first absorbent gel film and/or at least one of the at least one second absorbent gel film comprises pores and/or cavities matched in shape and size to one or more target analytes.

11. The FPSE of claim 1, wherein the first absorbent gel film and the at least one second absorbent gel films are stacked from the binding gel film.

12. The FPSE of claim 1, wherein the first absorbent gel film and the at least one second absorbent gel film are bound to a plurality of portions of the binding gel film.

13. A method of preparing a FPSE according to claim 1, comprising:
providing a flexible fabric;
depositing a first sol on a surface of the flexible fabric;
curing the first sol into a binding gel film;
optionally removing any unreacted portions of the first sol or non-bound side products formed during curing from the binding gel film;
depositing at least one second sol on a surface of the binding gel film;
curing the at least one second sol into a first absorbent gel film and optionally at least one second absorbent gel film; and
optionally removing any unreacted portions of the at least one second sol or non-bound side products formed during curing from the first absorbent gel film and any of the at least one second absorbent gel film.

14. The method of preparing a FPSE of claim 13, wherein the depositing at least one second sol comprises sequential depositing as a plurality of layers.

15. The method of preparing a FPSE of claim 13, wherein the depositing at least one second sol comprises ink-jet printing or any other process that places the first absorbent gel film and the at least one second absorbent gel film on different portions of the flexible fabric.

16. The method of preparing a FPSE of claim 13, wherein curing comprises an acid or a base catalyzed hydrolysis and condensation.

17. The method of preparing a FPSE of claim 16, further comprising an addition or polyaddition reaction catalyzed by an acid, a base, or a free radical initiator.

18. A method of sampling a target analyte, comprising:
providing a FPSE according to claim 1, wherein each of the first absorbent gel film and, optionally, the at least one second absorbent gel film is absorbent of at least one target analyte;
contacting the FPSE with an environment suspected of containing the target analyte; and
separating the FPSE from the environment suspected of containing the target analyte, wherein at least a portion of the target analyte contained in the environment suspected of containing the target analyte is absorbed in the FPSE.

19. The method of sampling a target analyte of claim 18, wherein the environment suspected of containing the target analyte comprises a gas, a liquid, or a surface of a solid.

20. The method of sampling a target analyte of claim 18, wherein contacting comprises suspension in a gaseous environment, immersion in a liquid environment, forcing the flow of a gaseous or liquid environment against or through the surface of the FPSE, wiping a liquid environment from a solid surface with the FPSE, or placing at least a portion of the FPSE on a portion of a solid surface.

21. A method of analyzing for a target analyte, comprising:
  providing a FPSE according to claim 1, wherein the first absorbent gel film and, optionally, the at least one second absorbent gel film is absorbent of at least one target analyte;
  contacting the FPSE with an environment suspected of containing the target analyte;
  separating the FPSE from the environment suspected of containing the target analyte, wherein at least a portion of the target analyte contained in the environment suspected of containing the target analyte is absorbed in the FPSE to form an analyte comprising FPSE;
  placing the analyte comprising FPSE in a removal container;
  adding a solvent or a solution to the removal container to form an analyte solution or heating and/or evacuating the removal container connected to a volatiles trap or an inlet of an analytical instrument; and
  introducing the analyte solution or contents of the volatile trap through an inlet of an analytical instrument.

22. The method of claim 21, wherein the analytical instrument is a GC, LC, IMS, capillary electrophoresis unit, or mass spectrometry.

* * * * *

UNITED STATES PATENT AND TRADEMARK OFFICE
CERTIFICATE OF CORRECTION

| | |
|---|---|
| PATENT NO. | : 9,557,252 B2 |
| APPLICATION NO. | : 15/069430 |
| DATED | : January 31, 2017 |
| INVENTOR(S) | : Abuzar Kabir et al. |

Page 1 of 1

It is certified that error appears in the above-identified patent and that said Letters Patent is hereby corrected as shown below:

In the Specification

Column 9,
Line 53, "removal contain is" should read --removal container is--.

In the Claims

Column 11,
Lines 51-52, "aryl groups phenyl groups" should read --aryl groups, phenyl groups--.

Signed and Sealed this
First Day of August, 2017

Joseph Matal
*Performing the Functions and Duties of the*
*Under Secretary of Commerce for Intellectual Property and*
*Director of the United States Patent and Trademark Office*